US006415470B1

(12) United States Patent
Ramrattan

(10) Patent No.: US 6,415,470 B1
(45) Date of Patent: Jul. 9, 2002

(54) LOTION APPLICATOR

(76) Inventor: Benedict L. Ramrattan, 7104 NW. 16th St., Plantation, FL (US) 33313

( * ) Notice: Subject to any disclaimer, the term of this patent is extended or adjusted under 35 U.S.C. 154(b) by 13 days.

(21) Appl. No.: 09/693,918

(22) Filed: Oct. 20, 2000

(51) Int. Cl.[7] ......................... A47L 25/00; A61M 35/00
(52) U.S. Cl. ..................... 15/144.4; 15/209.1; 15/244.2
(58) Field of Search ............................ 15/144.1, 144.3, 15/144.4, 209.1, 210.1, 244.1, 244.2

(56) References Cited

U.S. PATENT DOCUMENTS

| | | | | |
|---|---|---|---|---|
| 4,299,005 | A | | 11/1981 | Brown |
| 4,381,766 | A | * | 5/1983 | Avolio |
| 5,003,659 | A | * | 4/1991 | Paepke |
| 5,360,111 | A | | 11/1994 | Arispe |
| 5,419,015 | A | * | 5/1995 | Garcia |
| 5,437,372 | A | * | 8/1995 | Per-Lee |
| 5,493,749 | A | | 2/1996 | Zayas |
| 5,659,916 | A | * | 8/1997 | Beatty et al. |
| 5,671,497 | A | * | 9/1997 | Abdo |
| 5,692,261 | A | * | 12/1997 | Lops |
| D394,328 | S | | 5/1998 | Palumbo |
| 5,862,565 | A | * | 1/1999 | Lundstedt |
| 6,092,254 | A | * | 7/2000 | Kay |
| 6,240,590 | B1 | * | 6/2001 | Nesbit |

* cited by examiner

*Primary Examiner*—Terrence R. Till

(57) ABSTRACT

A lotion applicator for aiding a user in applying lotions to hard to reach areas. The lotion applicator includes a head assembly that includes a backing member and a pad that can be removed from the backing member. The handle extends from the head assembly and includes a gripping portion designed to be grasped by a hand.

18 Claims, 2 Drawing Sheets

LOTION APPLICATOR

BACKGROUND OF THE INVENTION

1. Field of the Invention

The present invention relates to lotion applicators and more particularly pertains to a new lotion applicator for aiding a user in applying lotions to hard to reach areas.

2. Description of the Prior Art

The use of lotion applicators is known in the prior art. More specifically, lotion applicators heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,360,111; U.S. Pat. No. 4,299,005; U.S. Pat. No. 4,381,766; U.S. Pat. No. 5,671,497; U.S. Pat. No. Des. 394,328; and U.S. Pat. No. 5,493,749.

While these devices fulfill their respective, particular objectives and requirements, the aforementioned patents do not disclose a new lotion applicator. The inventive device includes a head assembly that includes a backing member and a pad that can be removed from the backing member. The handle extends from the head assembly includes a gripping portion designed to be grasped by a hand.

In these respects, the lotion applicator according to the present invention substantially departs from the conventional concepts and designs of the prior art, and in so doing provides an apparatus primarily developed for the purpose of aiding a user in applying lotions to hard to reach areas.

SUMMARY OF THE INVENTION

In view of the foregoing disadvantages inherent in the known types of lotion applicators now present in the prior art, the present invention provides a new lotion applicator construction wherein the same can be utilized for aiding a user in applying lotions to hard to reach areas.

The general purpose of the present invention, which will be described subsequently in greater detail, is to provide a new lotion applicator apparatus and method which has many of the advantages of the lotion applicators mentioned heretofore and many novel features that result in a new lotion applicator which is not anticipated, rendered obvious, suggested, or even implied by any of the prior art lotion applicators, either alone or in any combination thereof.

To attain this, the present invention generally comprises a head assembly that includes a backing member and a pad that can be removed from the backing member. The handle extends from the head assembly and includes a gripping portion designed to be grasped by a hand.

There has thus been outlined, rather broadly, the more important features of the invention in order that the detailed description thereof that follows may be better understood, and in order that the present contribution to the art may be better appreciated. There are additional features of the invention, that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart. from the spirit and scope of the present invention. Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new lotion applicator apparatus and method which has many of the advantages of the lotion applicators mentioned heretofore and many novel features that result in a new lotion applicator which is not anticipated, rendered obvious, suggested, or even implied by any of the prior art lotion applicators, either alone or in any combination thereof.

It is another object of the present invention to provide a new lotion applicator, which may be easily and efficiently manufactured and marketed.

It is a further object of the present invention to provide a new lotion applicator, which is of a durable and reliable construction.

An even further object of the present invention is to provide a new lotion applicator which is susceptible of a low cost of manufacture with regard to both materials and labor, and which accordingly is then susceptible of low prices of sale to the consuming public, thereby making such lotion applicator economically available to the buying public.

Still yet another object of the present invention is to provide a new lotion applicator which provides in the apparatuses and methods of the prior art some of the advantages thereof, while simultaneously overcoming some of the disadvantages normally associated therewith.

Still another object of the present invention is to provide a new lotion applicator for aiding a user in applying lotions to hard to reach areas.

Yet another object of the present invention is to provide a new lotion applicator which includes a head assembly that has a backing member and a pad that can be removed from the backing member. The handle extends from the head assembly and includes a gripping portion designed to be grasped by a hand.

Still yet another object of the present invention is to provide a new lotion applicator that eliminates the need to ask for assistance from another individual as well as helps a user avoid painful or uncomfortable stretching and bending.

Even still another object of the present invention is to provide a new lotion applicator that frees hands of oily residue and increases hygiene due to the disposable nature of the applicator pads.

These together with other objects of the invention, along with the various features of novelty which characterize the invention, are pointed out with particularity in the claims annexed to and forming a part of this disclosure. For a better understanding of the invention, its operating advantages and the specific, objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
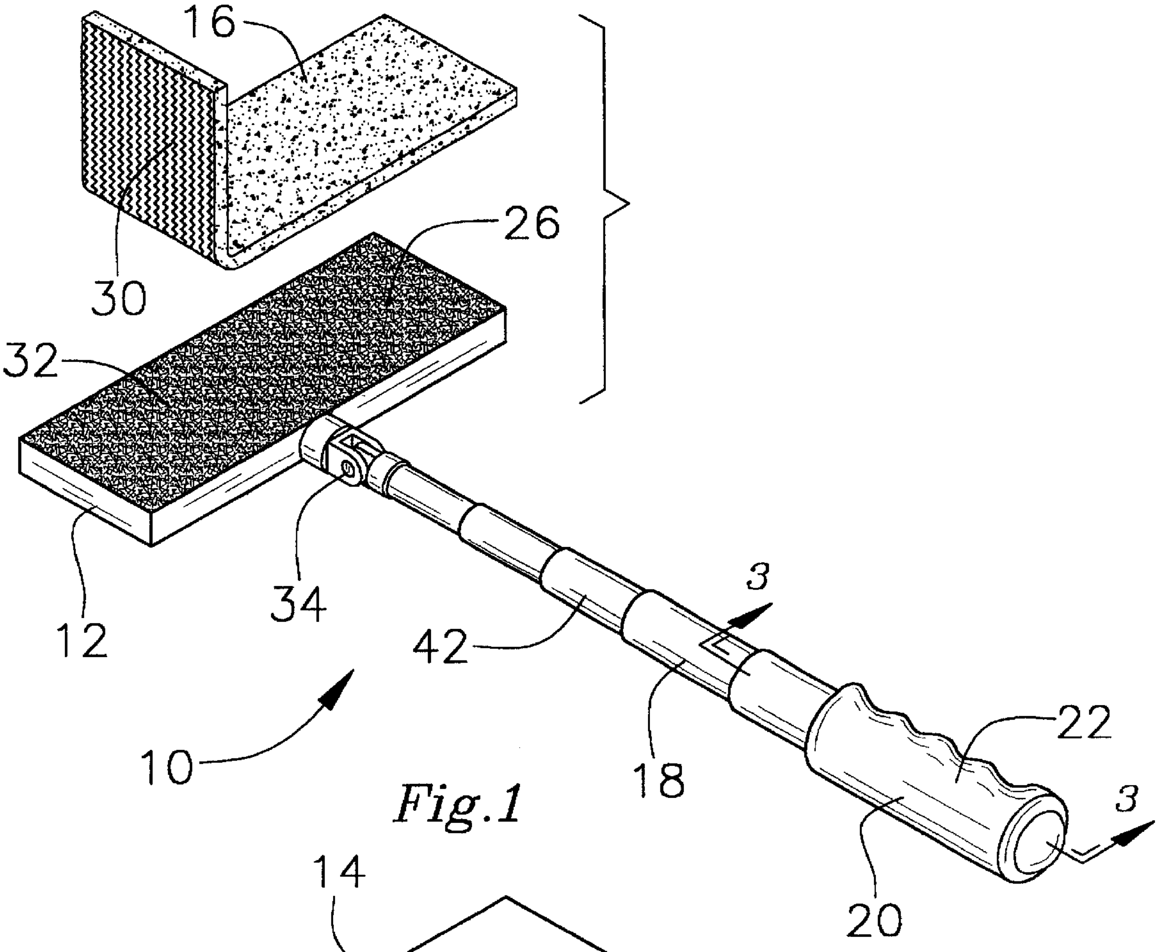
FIG. 1 is a bottom perspective view of a new lotion applicator according to the present invention.
Figure 2:
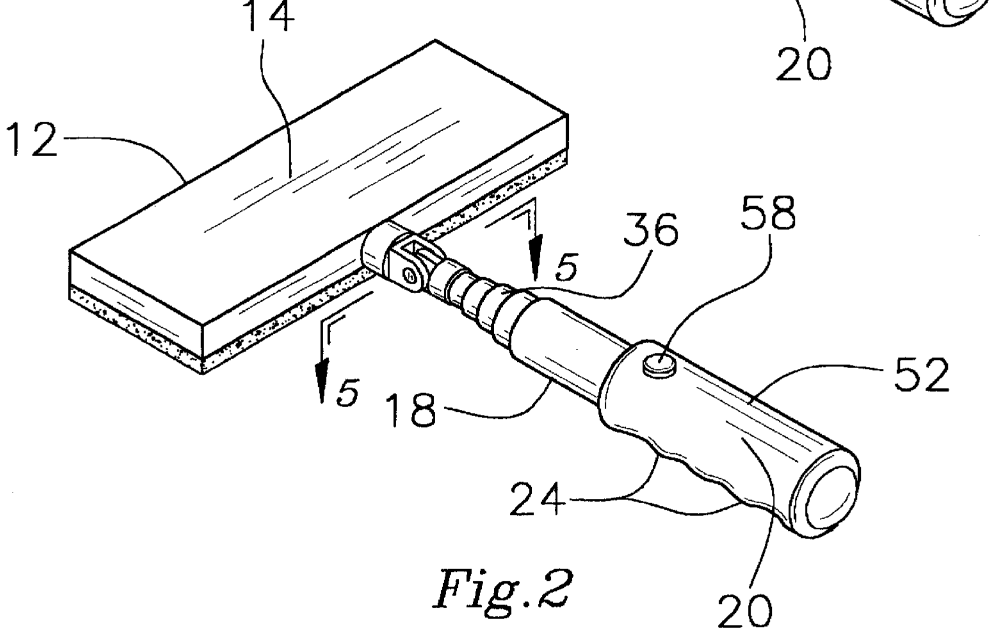
FIG. 2 is a top view of the present invention.
Figure 3:
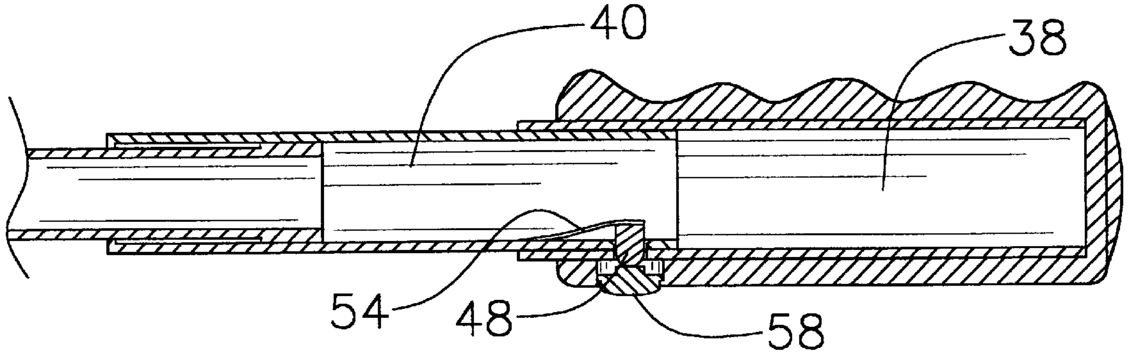
FIG. 3 is a side view of the present invention.
Figure 4:
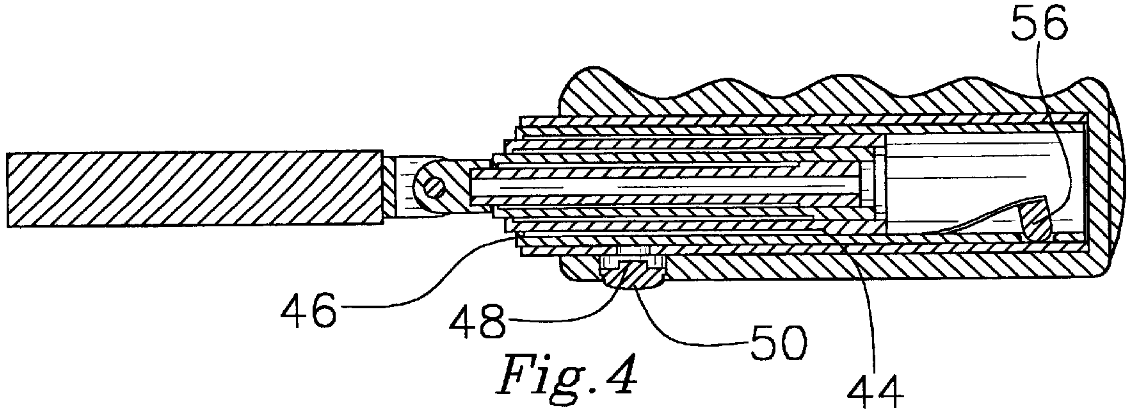
FIG. 4 is a side view of the present invention.
Figure 5:
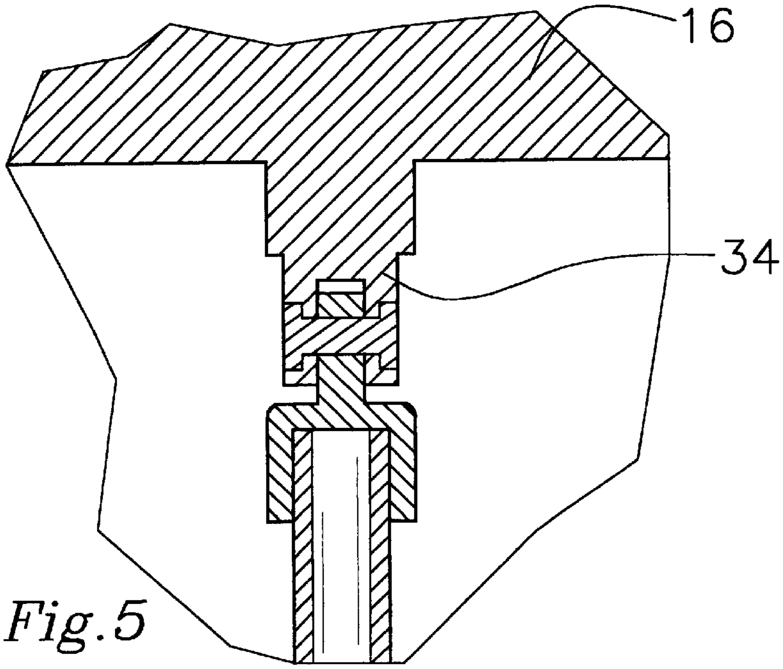
FIG. 5 is cutaway view of the present invention.

With reference now to the drawings, and in particular to FIGS. 1 through 5 thereof, a new lotion applicator embodying the principles and concepts of the present invention and generally designated by the reference numeral 10 will be described.

As best illustrated in FIGS. 1 through 5, the lotion applicator 10 generally includes a head assembly 12 that includes a backing member 14 and a pad 16 that can be removed from the backing member 14. A handle 18 extends from the head assembly 12 that includes a gripping portion 20 designed to be grasped by a hand.

The head assembly 12 includes a backing member 14 coupled to the telescopic handle 18 and a pad member 16 coupled to a face of the backing member 14. A grip cover 22 coupled to the handle 18 over the gripping portion 20. The grip cover 22 includes a plurality of indentations 24 for facilitating comfortable gripping of the grip cover 22.

A first portion 26 of hook and loop fastener 28 is coupled to *the face of the backing member 14, the first portion 26 of hook and loop fastener 28 is engaged to the pad member 16 whereby the pad member 16 can be removed from the backing member 14.

The pad member 16 is absorbent whereby the pad member 16 is designed for absorbing lotion placed on the pad member 16 for facilitating even spreading of the lotion by the pad member 16.

A second portion 30 of the hook and loop fastener 28 is coupled to a face of the pad member 16. The second portion 30 of hook and loop fastener 28 is complimentary to the first portion 26 of hook and loop fastener 28 whereby the pad member 16 can be removed from the backing member 14.

The backing member 14 includes an attachment portion 32, the attachment portion 32 is coupled to the handle 18, and the attachment portion 32 includes a swivel joint 34 whereby the backing member 14 is free to swivel relative to the handle 18.

The handle 18 includes a plurality of coaxially positioned nested tube members 36; each of the tube members 36 is coupled to an adjacently positioned tube member. The plurality of tube members 36 includes a first end member 38, a second end member 40, and a plurality of end members.

The gripping portion 20 is positioned on the first end member 38. Each of the medial members 42 includes a ridge portion 44 for abutting a lip portion 46 of an adjacently positioned tube member when the handle 18 is in an extended position. The first end member 38 includes an aperture 48.

The grip member. 52 includes a hole 50 positioned on a side opposite the indentations 24, the hole 50 is alignable with the aperture 48 when the grip member 52 is coupled to the handle 18 to cover the gripping portion 20.

A medial member 42 adjacent the first end member 38 includes a biasing assembly 54, the biasing assembly 54 includes a end portion 56 that can be positioned for extending through the aperture 48 when the medial member 42 adjacent the first end member 38 is in an extended position.

A button member 58 is coupled to the first end member 38 and covers the aperture 48 such that the end portion 56 of the biasing assembly 54 biases the button member 58 outwardly when the end member engages the aperture 48. The button member 58 is depressible into the first end member 38 whereby the end portion 56 is disengaged from the aperture 48 when the button 58 is depressed.

In use, a user would extend the handle and apply a lotion to the applicator pad and use the lotion applicator system to apply lotion in hard to reach areas.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A lotion applicator comprising:

a head assembly, said head assembly including a backing member and a pad removably coupled to said backing member;

a handle extending from the head assembly;

said handle having a gripping portion adapted for being grasped by a hand;

said handle including a plurality of coaxially positioned nested tube members, each of said tube members being coupled to an adjacently positioned tube member;

said plurality of tube members including a first end member, a second end member, and a plurality of end members;

said gripping portion being positioned on said first end member; and each of said medial members having a ridge portion for abutting a lip portion of an adjacently positioned tube member when said handle is in an extended position.

2. The lotion applicator of claim 1, further comprising:

said head assembly including a backing member coupled to said handle and a pad member coupled to a face of said backing member.

3. The lotion applicator of claim 2, further comprising:

a first portion of hook and loop fastener coupled to said face of said backing member, said first portion of hook and loop fastener being engageable to said pad member whereby said pad member is removably couplable to said backing member.

4. The lotion applicator of claim 3, further comprising:

a second portion of hook and loop fastener, said second portion of hook and loop fastener being coupled to a face of said pad member, said second portion of hook and loop fastener being complimentary to said first portion of hook and loop fastener whereby said pad member is removably couplable to said backing member.

5. The lotion applicator of claim 2, further comprising:

said pad member being absorbent whereby said pad member is adapted for absorbing lotion placed on said pad member for facilitating even spreading of the lotion by the pad member.

6. The lotion applicator of claim 2, further comprising:

said backing member including an attachment portion, said attachment portion being coupled to said handle, said attachment portion including a swivel joint whereby said backing member is free to swivel relative to said handle.

7. The lotion applicator of claim 1, further comprising: said handle being telescopic.

8. The lotion applicator of claim 1, further comprising:

a grip cover coupled to said handle over said gripping portion, said grip cover having a plurality of indentations for facilitating comfortable gripping of said grip cover.

9. A lotion applicator comprising:

a head assembly, said head assembly including a backing member and a pad removably coupled to said backing member;

a handle extending from the head assembly; and said handle having a gripping portion adapted for being grasped by a hand;

said handle including a plurality of coaxially positioned nested tube members, each of said tube members being coupled to an adjacently positioned tube member;

said plurality of tube members including a first end member and a plurality of end members;

said gripping portion being positioned on said first end member;

said first end member having an aperture;

a medial member adjacent said first end member having a biasing assembly, said biasing assembly having a end portion, said end portion being positioned for extending through said aperture when said medial member adjacent said first end member is in an extended position.

10. The lotion applicator of claim 9, further comprising:

a button member coupled to said first end member, said button member covering said aperture such that said end portion of said biasing assembly biases said button portion outwardly when said end member engages said aperture, said button member being depressible into said first end member whereby said end portion is disengageable from said aperture when said button is depressed.

11. The lotion applicator of claim 9, further comprising:

said head assembly including a backing member coupled to said handle and a pad member coupled to a face of said backing member.

12. The lotion applicator of claim 11, further comprising:

a first portion of hook and loop fastener coupled to said face of said backing member, said first portion of hook and loop fastener being engageable to said pad member whereby said pad member is removably couplable to said backing member.

13. The lotion applicator of claim 12, further comprising:

a second portion of hook and loop fastener, said second portion of hook and loop fastener being coupled to a face of said pad member, said second portion of hook and loop fastener being complimentary to said first portion of hook and loop fastener whereby said pad member is removably couplable to said backing member.

14. The lotion applicator of claim 11, further comprising:

said pad member being absorbent whereby said pad member is adapted for absorbing lotion placed on said pad member for facilitating even spreading of the lotion by the pad member.

15. The lotion applicator of claim 11, further comprising:

said backing member including an attachment portion, said attachment portion being coupled to said handle, said attachment portion including a swivel joint whereby said backing member is free to swivel relative to said handle.

16. The lotion applicator of claim 9, further comprising:

said handle being telescopic.

17. The lotion applicator of claim 9, further comprising:

a grip cover coupled to said handle over said gripping portion, said grip cover having a plurality of indentations for facilitating comfortable gripping of said grip cover.

18. A lotion applicator comprising:

a head assembly, said head assembly including a backing member and a pad removably coupled to said backing member;

a handle extending from the head assembly;

said handle having a gripping portion adapted for being grasped by a hand;

said head assembly including a backing member coupled to said handle and a pad member coupled to a face of said backing member;

said handle being telescopic;

a grip cover coupled to said handle over said gripping portion, said grip cover having a plurality of indentations for facilitating comfortable gripping of said grip cover;

a first portion of hook and loop fastener coupled to said face of said backing member, said first portion of hook and loop fastener being engageable to said pad member whereby said pad member is removably couplable to said backing member;

said pad member being absorbent whereby said pad member is adapted for absorbing lotion placed on said pad member for facilitating even spreading of the lotion by the pad member;

a second portion of hook and loop fastener, said second portion of hook and loop fastener being coupled to a face of said pad member, said second portion of hook and loop fastener being complimentary to said first portion of hook and loop fastener whereby said pad member is removably couplable to said backing member;

said backing member including an attachment portion, said attachment portion being coupled to said handle, said attachment portion including a swivel joint whereby said backing member is free to swivel relative to said handle;

said handle including a plurality of coaxially positioned nested tube members, each of said tube members being coupled to an adjacently positioned tube member;

said plurality of tube members including a first end member, a second end member, and a plurality of end members;

said gripping portion being positioned on said first end member;

each of said medial members having a ridge portion for abutting a lip portion of an adjacently positioned tube member when said handle is in an extended position;

said first end member having an aperture;

said grip member having a hole positioned on a side opposite said indentations, said hole being alignable with said aperture when said grip member is coupled to said handle to cover said gripping portion;

a medial member adjacent said first end member having a biasing assembly, said biasing assembly having a end portion, said end portion being positioned for extending through said aperture when said medial member adjacent said first end member is in an extended position; and a button member coupled to said first end member, said button member covering said aperture such that said end portion of said biasing assembly biases said button portion outwardly when said end member engages said aperture, said button member being depressible into said first end member whereby said end portion is disengagable from said aperture when said button is depressed.

* * * * *